United States Patent [19]

Gamble et al.

[11] Patent Number: 4,497,791

[45] Date of Patent: Feb. 5, 1985

[54] METHOD FOR LABELING PHAGOCYTIC CELLS

[75] Inventors: Ronald C. Gamble, Pasadena; George W. Tin, Arcadia; Lawrence E. Williams, San Dimas, all of Calif.

[73] Assignees: Vestar Research Incorporated, Pasadena; City of Hope National Medical Center, Duarte, both of Calif.

[21] Appl. No.: 465,502

[22] Filed: Feb. 10, 1983

[51] Int. Cl.$^3$ .................... A61K 43/00; A61K 49/00
[52] U.S. Cl. .......................................... 424/1.1; 424/9
[58] Field of Search .................................... 424/1.1, 9

[56] References Cited
PUBLICATIONS

McAfee et al., J. Null. Med., 17, (1976), 480–487, 488–492.
Thakur et al., J. Lab. Clin. Med., 89, (1977), 217–28.
Segal, The Lancet, vol. II, (1981), #8240, pp. 230–232.

*Primary Examiner*—Christine M. Nucker
*Attorney, Agent, or Firm*—Lyon & Lyon

[57] ABSTRACT

Described herein is a process for labeling leukocytes and other phagocytic cells with labeled micellular particles involving incubating the cells with the micellular particles. Also described is a process for detecting the locus of an infection by administering to a subject leukocytes radiolabeled by incubation with labeled micellular particles followed by scanning the subject to detect the locus of radiation emitted by the particles.

25 Claims, No Drawings

METHOD FOR LABELING PHAGOCYTIC CELLS

BACKGROUND

The invention herein concerns the labeling of cells, usually in the bloodstream, which are capable of phagocytosis. More specifically, the invention provides a method for supplying a label to the cells by taking advantage of their phagocytic properties with respect to suitably labeled micellular particles such as vesicles which have surface amino groups. In the method of the invention, the label is carried to and entrapped in the phagocytic cell by subjecting these micellular particles to endocytosis.

There is an extensive technology relating to the problem of labeling specific types of cells so that they can be traced and located within an organism. A recent survey of the state of the art concerning radioactive labels, particularly, the gamma-emitter indium-111 (In-111), is summarized in *Indium-111 Labeled Neutrophils, Platelets and Lymphocytes*, Proceedings of the Yale Symposium, New York City, N.Y., Sept. 14 and 15, 1979, Trivirum Publishing Company, N.Y. (1980).

One approach that has frequently been used for labeling cells is that of isolating the cells desired to be labeled, and then supplying the labeling material only to these cells. This approach, of course, has the inherent disadvantage of requiring clean separation of the desired cells from other components associated with them, which, at best, constitutes an additional step. Even the relatively straightforward separation of blood into red blood cells and plasma is a troublesome step, if this technique is to be used for in vivo diagnosis, because the performance of this step mandates a longer residence time for the cells outside the body. Other separations are even more subtle. For example, it is particularly difficult to separate blood monocytes from neutrophils as well as from lymphocytes (ibid, page 5). The technique in common use today for introducing In-111 to cells, which employs indium complexed with 8-hydroxy-quinoline (oxine), is non-specific with respect to these cells and requires prior isolation if one cell type is to be targeted.

An alternative approach has been to use specific labeling agents which are known to prefer a particular type of cell. An example is the use of $^{32}p$ diisopropylfluorophosphate ($DF^{32}p$) for the specific binding of neutrophils in preference to other blood components (ibid, page 1). However, since this reagent is a beta-emitter, a tracing method which uses this label is inherently less sensitive than any method which uses indium-111. Other commonly used labels include chromium-51, gallium-67 and radioactive isotopes of iodine. All of these labels suffer from the non-specificity exhibited by their known chemically combined forms, as well as from other problems.

The following references provide background for the invention and are incorporated into the herein application by reference.

1. Burleson, R. L., Johnson, M. C. & Head, H. (1973) *Ann. Surg.*, 178, 446.Scintigraphic demonstration of experimental abscesses with intravenous $^{67}Ga$ citrate and $^{67}Ga$ labeled blood leukocytes.
2. Burleson, R. L., Johnson, M. C. & Head, H. (1974) *J. Nucl. Med.*, 15, 98. In vitro and in vivo labeling of rabbit blood leukocytes with $^{67}Ga$ citrate.
3. Forstrom, L., L. Gomez, B. Weiblen, D. Hoogland, J. McCullough, & M. Loken (1978) *J. Nucl. Med.*, 19, 672. Clinical use of indium-111 oxine labeled leukocytes in the detection of inflamation or abscess.
4. Zakhireh, B., M. L. Thakur, H. L. Malech, M. S. Cohen, A. Gottschalk, & R. K. Root (1979) *J. Nucl. Med.*, 20, 741. Indium-111-labeled human polymorphonuclear leukocytes: Viability, random migration, chemotaxis, bactericidal capacity, and ultrastructure.
5. Dutcher, J. P., C. A. Schiffer & G. S. Johnson (1981) *N. Eng. J. Med.*, 304, 586. Rapid migration of indium-111-labeled granulocytes to sites of infection.
6. Alavi, J. B., M. M. Staum & A. Alavi (1980) "In-111 for granulocyte labeling in neutropenic patients" in *Indium-111 Labeled Neutrophils, Platelets and Lymphocytes*, eds. M. L. Thakur & A. Gottschalk (Trivirum Publishing Co., New York) pp. 41–50.
7. Forstrom, L. A., B. J. Weiblen, L. Gomez, N. L. Ascher, D. R. Hoogland, M. K. Loken, & J. McCullough (1980) "Indium-111-oxine-labeled leukocytes in the diagnosis of occult inflammatory disease" in *Indium-111 Labeled Neutrophils, Platelets and Lymphocytes*, eds. M. L. Thakur & A. Gottschalk (Trivirum Publishing Co., New York) pp. 123–140.
8. Goodwin, D. A., P. W. Doherty & I. R. McDougall (1980) "Clinical use of In-111-labeled white cells: An analysis of 312 cases" in *Indium-111 Labeled Neutrophils, Platelets and Lymphocytes*, eds. M. L. Thakur & A. Gottschalk (Trivirum Publishing Co., New York) pp. 131–150.
9. Thakur, M. L., J. P. Lavender & R. N. Arnot (1977) *J. Nucl. Med.*, 18, 1014. Indium-111-labeled autologous leukocytes in man.
10. Mauk, M. R., R. C. Gamble & J. D. Baldeschwieler (1980) *Science*, 207, 309. Vesicle targeting: Time release and specificity for the leukocytes system in by subcutaneous injection.
11. Mauk, M. R., R. C. Gamble & J. D. Baldeschwieler (1980) *Proc. Natl. Acad. Sci. USA*, 77, 4430. Targeting of lipid vesicles: Specificity of carbohydrate receptor analogues for leukocytes in mice.
12. Wu, P. S., G. W. Tin & J. D. Baldeschwieler (1981) *Proc. Natl. Acad. Sci. USA*, 78, 2033. Phagocytosis of carbohydrate-modified phospholipid vesicle by macrophage.

Hereinafter, citation to these references shall be done by inserting the number of a cited reference within a parenthesis.

The tracing of phagocytic cells is of particular importance because they tend to accumulate at the sites of infections and abscesses. At the present time, a significant number of the numerous abdominal surgeries performed annually to repair wounds and for corrective purposes result in occult infections which require intensive care. Also, the formation of microabscesses at the interface of an organ transplant is an indicator of the first stages of tissue rejection. It is known, of course, that certain white blood cells accumulate at these infection sites, and attempts have been made to use leukocyte labeling to permit detection of these accumulations (1, 2). Since the known techniques are non-specific, use of the radiolabeling techniques discussed above to detect these occult infections necessitates a prior separation of leukocytes by isolating blood from the patient, separating the leukocyte rich plasma from the red blood cells by centrifugation, incubating the plasma with, for example, In-111 oxine, and then reinjecting the labeled plasma into the patient. Gamma imaging of the patient is used to locate aggregations of the labeled leukocytes which are attracted to the site of an infection (3, 4, 5).

However, this approach has not solved the problem of non-specificity which has been experienced with other reagents because of background radiation due to an accumulation of the In-111 in undesired locations (6, 7, 8). This accumulation occurs either because the In-111 was not exclusively attached to the leukocyte in the first place, (but also, for example, to the red blood cells) or because a portion of the In-111 becomes deposited in the liver, spleen and other organs by virtue of damage to carrier leukocytes occurring in the separation or labeling processes, or both. Further, the dumping of In-111 onto non-targeted sites by damaged leukocytes results in retention of radioactivity at these locations which has the consequence of increasing the patient's exposure to radiation (9).

Other difficulties have been found. The diminution of the phagocytic and chemotactic abilities of the leukocytes which have been exposed to the reagents used for labeling has also reduced the effectiveness of the method (4, 5). Further, there is the general disadvantage of a 2 to 3 hour residence time for the leukocytes outside the body of the patient because of the necessity for plasma separation.

The method of the present invention overcomes these difficulties by providing a more effective technique for specifically labeling leukocytes, either while outside the patient's body or by injection, which uses micellular particles such as vesicles as a carrier for a label. Significantly, the method does not require the separation of blood into its various cell types even though partial or complete separation is not inconsistent with the method of the invention and may have advantages in certain applications.

The invention takes advantage of, and extends, the observed property of incorporating an extended amine on a micelle's surface to cause aggregation of polymorphonuclear leukocytes when injected subcutaneously (10, 11) and to enhance phagocytosis by peritoneal macrophages in vitro (12).

In the process of the invention, rather than employing oxine, the In-111 (or other label) is enclosed in, or otherwise bound to the micellular particles which can be phagocytosed by the leukocytes but which do not bond or otherwise become fixed to other cells, thereby permiting and encouraging the incorporation of the label into the phagocytic cells, which, in turn seek out and accumulate at sites of occult infection. Vesicles are particularly preferred as the micellular particle.

SUMMARY OF THE INVENTION

The present invention, in one aspect, relates to a method of specifically labeling cells which are capable of phagocytosis by providing a micellular particle which carries a label, which carrier micelle is specific to phagocytic cells. When so labeled, these cells are particularly useful in the detection of occult infections. In yet another aspect, the invention relates to labeling phagocytic cells, injecting them into a subject, and detecting the presence of the labeled cells at the site of accumulation.

In a particularly preferred embodiment of the invention, vesicles which contain aminosaccharides or other extended amines or amino moiety on their surfaces are provided with radiation emitting cations, for example, $In^{+3}$-111 or other gamma emitter, by encapsulation techniques which permit trapping of the label inside the vesicle. The vesicle formulation is then incubated with leukocytes or with whole blood, either in vitro or by injection, or, of course, with any suitable cell or cell fraction which contains phagocytic cells. The chemotactic properties of the carrier vesicles provide sufficient specificity for leukocytes to enhance aggregation of white blood cells at the expense of other components. More important, they are engulfed by the desired phagocytic cells, and thus removed from the medium. Any undesired associations external to other cells can then be disrupted by shifting the equilibrium using increased concentrations of mimicing amines.

DETAILED DESCRIPTION

Definitions and Abbreviations

As used herein, the term "phagocytic cells" refers to those white blood cells (leukocytes) which are capable of engulfing intruders. There appears to be no rigid classification system for leukocytes which results in completely mutually exclusive categories. However, those cells which are capable of phagocytosis include neutrophils, monocytes and other macrophages. Phagocytic cells are not believed to include lymphocytes, platelets, or erythrocytes. In the invention herein, "phagocytic cells" is used to encompass any cell which is capable of consuming foreign substances, whether these cells are circulating in the blood stream or find substantial residence time in a particular organ for appreciable periods.

"Micellular particle" and "micelles" refer to particles which result from aggregations of amphiphilic molecules. In this invention preferred amphiphiles are biological lipids.

"Vesicle" refers to a micelle which is in a generally spherical form, often obtained from a lipid which forms a bilayered membrane and is referred to as a "liposome". Methods for forming these vesicles are, by now, very well known in the art. Typically, they are prepared from a phospholipid, for example, distearoyl phosphatidylcholine or lecithin, and may include other materials such as neutral lipids, and also surface modifiers such as positively or negatively charged compounds. Depending on the techniques for their preparation, the envelope may be a simple bilayered spherical shell (a unilamellar vesicle) or may have multiple layers within the envelope (multi-lamellar vesicles).

"Extended amine" refers to molecules having an amine moiety which are capable of incorporation or association into the surfaces of vesicles or other micelles and, which, when incorporated thereon, provide an amine function that is extended approximately 5–15 angstroms, preferably about 10 angstroms, beyond the surface of the micelles. In the case of vesicles, It appears that the appropriate molecular design comprises a hydrophobic portion which serves to anchor the molecule within the vesicular bilayer, and a linking portion which is at least mildly hydrophilic and which spans the requisite distance between the hydrophobic region and the amino functional group. The hydrophilicity is apparently required to prevent the link from internalizing within the bilayer also and thus serves to "extend" the amine from the surface. An example of a successful extended amine within the context of this invention is a 6-aminomannose cholesterol derivative such as, for example, 6-(5-cholesten-3-yloxy) hexyl 6-amino-6-deoxy-1-thio-D-manno-pyranoside. In this example, the cholesterol portion provides the hydrophobic moiety, while the amino mannose is relatively hydrophilic. Other embodiments are certainly also possible: other amino sugars attached to other cholesterol derivatives, for example, are equally suitable as alternative embodiments of the hydrophilic and hydrophobic portions. Polyamines and polyamino acids which can be bound covalently or associated by other means to the vesicle or other micelle surface may also be used.

"Occult infections" refer to infection sites which are concealed within the body and not evident from surface examination.

For simplicity, the following abbreviations, most of which are conventional will be used herein. They are, for convenience, listed here:

CHEMICAL NAMES

DSPC=distearyol phosphatidylcholine;
Ch=cholesterol;
AMS="6-aminomannose"=6-(5-cholesten-3-yloxy) hexyl-6-amino-6-deoxy-1-thio-D-mannopyranoside;
AML "6-aminomannitol", the corresponding reduced form of AMS;
A23187=the ionophore, [6S-(2S* 3S*,),8-(R*, 9 11]-5-methyl amino-2-3, 9, 11-trimethyl-8-[1-methyl-2-oxo-2-(1H-pyrrol-2-yl)3, 9, 11-ethyl]-1,7-dioxasporo [5.5] undec-2-yl]methyl]-4-benzoxazolecarboxylic acid;
NTA=nitrilotriacetic acid;
EDTA=ethylenediamine tetraacetic acid.

PARTICLES

PMN=polymorphonuclear leukocytes;
SUV=small unilamellar vesicles.

GENERAL

PBS buffer=A phosphate buffered saline solution comprising 5-10 mM phosphate and containing 0.9% sodium chloride, buffered to the specified pH, usually 7.4.

As already noted, the present invention is broadly directed to the labeling of phagocytic cells by means of micellular particles capable of specific phagocytosis which function as carriers for the label. Particularly preferred for use in the invention are phospholipid vesicles. The manner of their preparation and use is set forth in the following description of the preferred embodiment of the invention.

Preparation and Loading of Vesicles

Vesicles containing surface bound amines which are suitable for use in the invention are prepared by means known in the art, as set forth in U.S. Pat. No. 4,310,505, incorporated herein by reference. The basic vesicles are composed of DSPC, L-dipalmitoyl phosphatidyl choline (DPPC) or, less desirably, other phospholipids such as lecithin, and a neutral lipid, most conveniently Ch. The extended amine which is included in the vesicle preparation medium is preferably AMS or AML, but other compounds satisfying the criteria for an extended amine set forth hereinabove, may be used. In a typical preparation, a chloroform solution containing 20 μmol DSPC, 7.5 μmol Ch, 0.04 μmol A23187 and 2.5 μmol AMS is evaporated to dryness under nitrogen, and further dried under vacuum overnight. The resulting lipid film is then hydrated with 0.6 ml PBS buffer (pH 7.4 containing 1 mM of EDTA), and sonicated under nitrogen for 10 minutes with an Heat System sonicator equipped with a titanium microtip. The preparation is then annealed at 60° for 10 minutes and clarified by centrifugation at 300×G. The residue is discarded, and the supernatant containing the vesicles is separated from unencapsulated EDTA by chromatography over a 30 by 1.5 cm Sephadex G-50 column. Vesicles prepared in this manner have a mean diameter of less than 1,000 A°. Chelating agents other than EDTA can be used.

The vesicles are loaded with In-111 by the procedure set forth in U.S. Pat. No. 4,310,506, incorporated herein by reference. Typically, the incubation mixture comprises 500 μl vesicles, in PBS, 35 μl of 3.4 μM InCl$_3$ in 104 mM sodium citrate (pH 7.4) and 1-50 μl of In$^{+3}$-111 in 2 mM HCL. (The dilution caused by In$^{+3}$-111 solution is made up by an equal volume of double strength PBS.) EDTA is added to terminate loading by scavenging unincorporated In$^{+3}$-111.

Method for Labeling Phagocytic Cells

As mentioned above, in a preferred embodiment the present invention concerns specifically labeling phagocytic cells using vesicles, preferably SUVs, which have extended amines incorporated into their surfaces.

The vesicles with surface-contained extended amines are "loaded" to carry a material suitable for labeling the phagocytic cell, and then mixed with a solution containing the phagocytic cells desired to be labeled. Suitable labeling materials for incorporation within the vesicles include radioactive materials, particularly gamma emitters such as In-111, Ga-67, Tc-99M, Cr-51, I-125, and materials which are fluorescent or are otherwise detectable in in vitro applications of phagocytic cells. The phagocytic cells may be supplied in a mixture, such as whole blood, or if desired, in a more concentrated form, such as blood plasma. Blood, for example, is mixed with a citratedextrose or buffered heparin solution, and incubated at 25° to 39°, preferably around 34° to 37° for about 3 minutes to an hour, preferably around 30 minutes. The resulting labeled phagocytes may then, if desired, be recovered by centrifugation.

If the sample solution contains non-phagocytic cells, any non-specific, non-phagocytosed labeling may be removed by bringing the solution to a concentration of 0.5 to 3 M, preferably about 1 M, in an extended amine, either the same as that used in the surface of the vesicles, or another molecule of similar characteristics. This treatment serves to dissociate any vesicles which have been bound to the surface of non-phagocytic cells, and not engulfed by the vesicles, by shifting the equilibrium between associated and dissociated vesicles. The solution is then spun down to recover the labeled phagocytes. The supernatant, which contains soluble materials and free vesicles, is discarded.

Method for Detecting Occult Infections

In another aspect, this invention concerns utilizing the labeled phagocytic cells to detect occult infection. In the method of this invention, the vesicles prepared as described above or other labeled micellular particles are mixed with a solution containing the phagocytic cells, and the labeled phagocytes recovered as above.

The recovered cells are then resuspended and injected into the subject mammal. After several hours, the subject is examined with a whole body scanner designed to detect radiation which is preferably gamma radiation. Whole body images or images obtained by the scanning of individual parts of the body may be used for diagnostic purposes. The site of infection is then located by detection of areas which exhibit a high level of radiation.

In an alternative method of introducing the labeled micelles with the targeted phagocytes, an isotonic buffered suspension of the micelles is injected intravenously. In the case of vesicles, this approach does not permit use of equilibrium shift to dissociate non-phagocytosed superficially bound vesicles; however, the specificity conferred by the surface extended amine is sufficient to reduce background to a satisfactory level.

The following examples are intended to illustrate but not to limit the invention.

EXAMPLE I

The preferential uptake of radioactivity by leukocytes was shown by incubating radiolabeled vesicles with different blood preparations and control solutions as shown in Table 1.

Essentially, vesicles were prepared and loaded as described in U.S. Pat. No. 4,310,505 and U.S. Pat. No. 4,310,506, the disclosures of which are incorporated by reference, from DSPC, Ch, AMS and A23187 in the mole ratio of 2:0.5:0.5:0.004. Vesicles were formed by sonication in the presence of 1 mM EDTA in PBS (pH 7.4) and were then loaded with $In^{+3}$-111, at 1 millicurie per 10 mg of lipid.

Human blood (10 ml) was freshly drawn and stabilized with 0.5 ml heparin in PBS (1000 IU/ml). Washed red blood cells (RBC) were prepared by fractional centrifugation (800×g) using a 10 ml preformed 70% Percoll density gradient. Washed cells were resuspended in an equivalent volume of PBS. Plasma was simply the supernatant of centrifuged whole blood.

Each incubation mixture contained radiolabeled vesicles (1 mg lipid in approx 0.1 ml PBS) and either A) 2 ml PBS, B) 2 ml whole blood, C) 2 ml washed and resuspended RBC or D) 2 ml plasma. Following incubation for 30 minutes at 37° C., each test mixture was placed on a 10 ml preformed 70% Percoll density gradient and centrifuged at 800×g. Following fractionation those assigned fractions which would contain RBC's or leukocytes (whether or not those cells were actually present) were assayed for gamma activity. The results are shown in Table I.

TABLE I

| TEXT MIXTURE | Ratio of Radioactivity in leukocyte Fraction to Radioactivity in RBC Fraction |
|---|---|
| A Vesicles in PBS | 1.6 |
| B Vesicles + whole blood | 30.0 |
| C Vesicles + washed RBC | 1.2 |
| D Vesicles + Plasma | 2.7 |

The data indicate that the Percoll gradient introduced some bias in activity to the leukocyte fraction (A). (A value of 1.0 is expected because vesicles should distribute evenly, although some diffusion effects are possible). Vesicles incubated with either washed RBC (C) or plasma (D) altered that bias to a minor degree. Significantly, vesicles were taken up readily by leukocytes (B).

EXAMPLE II

The uptake of vesicles by leukocytes in whole canine blood is shown. Not only are high levels of radioactivity incorporated, but also the labeling efficiency is high.

Radiolabeled vesicles were prepared as in Example I. Freshly drawn and heparinized canine blood (2 ml samples) was incubated for 60 minutes at 37° C. with different amounts of vesicles, ranging from 10 to 250 μg lipid. Subsequently, the mixtures were centrifuged, separating the vesicles bound to cells in the pellet from the unbound vesicles in the plasma which was discarded. Cells resuspended with fresh plasma were added by pipet to 5 cc syringes filled with 1 g USP cotton. On washing with 30 ml PBS phagocytic leukocytes bind while RBC elutes off the column. Gamma activity associated with each fraction were assayed. Data are presented in Table II.

TABLE II

| g Vesicles added to whole blood (2 ml) | Ratio of Leukocyte activity vs RBC activity | Percent of total activity associated with Phagocytic Leukocytes |
|---|---|---|
| A 250 | 38 | 39 |
| B 100 | 33 | 65 |
| C 50 | 67 | 68 |
| D 10 | 26 | 43 |

It is readily apparent that both preferential labeling and a high absolute labeling level are possible for leukocytes. It should be noted that condition (C) represents the equivalent of 1 mg lipid vesicles used for labeling 40 ml blood, a volume presently used for the In-oxine labeling method. Typically, 1–3 mCi In-111 are used for gamma imaging. Loading vesicles at a specific activity of 1 mCi/mg lipid has been achieved, which is adequate to permit use of leukocytes with radiolabeled vesicles for imaging infectious sites.

Those skilled in the art will appreciate that this invention also comprehends loading vesicles or other micelles with agents other than In-111 which can be used to permit detection of the phagocytic cells or for other purposes. For example, a beta-emitter can be used for therapeutic applications. Other labels for in-vivo applications include antibodies or other physiologically active agents which desirably are delivered to sites of phagocytic cell concentration.

We claim:

1. A process for labeling cells comprising incubating cells capable of phagocytosis with labeled micellular particles having an amine on the surface thereof, for a time sufficient to permit uptake of the micellular particles by the cells.

2. A process according to claim 1 wherein the cells are leukocytes.

3. A process according to claim 2 wherein the micellular particles are vesicles.

4. The process according to claim 3 in which said vesicles contain an extended amine on their surface.

5. A process according to claim 3 wherein the extended amine is an aminosaccharide.

6. A process according to claim 5 wherein the aminosaccharide is a 6-aminomannose.

7. A process according to claim 6 wherein the 6-aminomannose is 6-(5-cholesten-3-yloxy)hexyl 6-amino-6-deoxy-1-thio-D-mannopyranoside.

8. A process according to claim 7 wherein the label is a radioactive element.

9. A process according to claim 8 wherein the radioactive element is a gamma emitter.

10. A process according to claim 9 wherein the gamma emitter is a cation.

11. A process according to claim 10 wherein the cation is $In^{+3}$-111.

12. A process according to claims 2 or 3 wherein the leukocytes are in whole blood.

13. A process according to claims 2 or 3 wherein the leukocytes have been separated from red blood cells.

14. A process for detecting the locus of an infection in a mammalian subject comprising:

(a) introducing to the mammal's bloodstream homologous leukocytes capable of phagocytosis labelled by incubating the leukocytes with radio-labelled micellular particles having an amine on the surface thereof, for a time sufficient to permit uptake of the micellular particles by phagocytosis; and (b) scanning the subject with means for detecting the locus of radiation emitted by the micellular particles.

15. A process according to claim 14 wherein the leukocytes are in whole blood.

16. A process according to claim 14 wherein the leukocytes have been separated from red blood cells.

17. A process according to claims 14, 15 or 16 wherein the leukocytes are obtained by withdrawing blood from the subject.

18. A process according to claim 17 wherein the micellular particles are vesicles.

19. The process of claim 18 in which said vesicles contain an extended amine on their surface.

20. A process according to claim 18 wherein the extended amine is an aminosaccharide.

21. A process according to claim 20 wherein the aminosaccharide is a 6-aminomannose.

22. A process according to claim 21 wherein the 6-aminomannose is 6-(5-cholesten-3-yloxy)hexyl 6-amino-6-deoxy-1-thio-D-mannopyranoside.

23. A process according to claims 14, 15 or 16 wherein the radiolabel is a gamma emitter.

24. A process according to claim 23 wherein the radiolabel is a cation.

25. A process according to claim 23 wherein the cation is $In^{+3}$-111.

* * * * *